United States Patent [19]

Fürbringer

[11] Patent Number: 5,886,196
[45] Date of Patent: Mar. 23, 1999

[54] METHOD OF CATALYZING CONDENSATION REACTIONS

[75] Inventor: Claude Fürbringer, Riehen, Sweden

[73] Assignee: Roche Vitamins Inc., Parsippany, N.J.

[21] Appl. No.: 768,680

[22] Filed: Dec. 18, 1996

[30] Foreign Application Priority Data

Jan. 12, 1996 [SE] Sweden ........................... 96/96

[51] Int. Cl.$^6$ ..................... C07D 317/06; C07D 323/02; C07D 493/10
[52] U.S. Cl. ............................. 549/213; 549/308
[58] Field of Search ................... 549/213, 308

[56] References Cited

U.S. PATENT DOCUMENTS 3,530,098 9/1970 Schweizer.
5,468,883 11/1995 Grafen et al..

FOREIGN PATENT DOCUMENTS 314 309    5/1989   European Pat. Off..
93/19057   9/1993   WIPO.

OTHER PUBLICATIONS

Kobayashi, H., et al., *Chemistry Letters,* XP002028082, pp. 1185–1186 (1982).
Hoaglin, R.I., et al., *J. Am. Chem. Soc.,* 80, 3069–3073 (1958).
Lamande, L., et al.,*J. Organometallic Chemistry,* 329, 1–29 (1987).

*Primary Examiner*—Johann Richter
*Assistant Examiner*—Taofiq A. Solola
*Attorney, Agent, or Firm*—George W. Johnston; Dennis P. Tramaloni; Joseph P. Kirk, Jr.

[57] ABSTRACT

Hydrogen bis(oxalato)borate of the formula

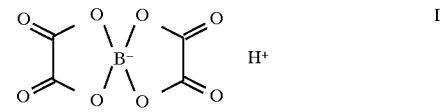

is used as a protonic acid catalyst in condensation reactions, such as Friedel-Crafts condensations, vinyl ether condensations of acetals with vinyl or propenyl ethers and acylations of phenols. The products of such condensations are, for example, dihydro-vitamin $K_1$ monobenzoate, d,l-α-tocopherol, various intermediates in the synthesis of carotenoids as well as d,l-α-tocopherol acetate. As a result of the use in accordance with the invention of hydrogen bis(oxalato)borate various disadvantages associated with the use of other protonic acid catalysts, e.g. problems with corrosion, toxicity and environmental contamination, are avoided. The novel catalyst has advantages with respect to selectivity, yields, amounts required as well as working up after completion of the respective condensation.

22 Claims, No Drawings

METHOD OF CATALYZING CONDENSATION REACTIONS

BACKGROUND OF THE INVENTION

The present invention is concerned with the use of hydrogen bis(oxalato)borate of the formula

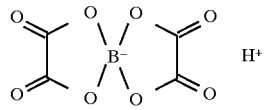

as a protonic acid catalyst in condensation reactions, such as Friedel-Crafts condensations, vinyl ether condensations of acetals with vinyl or propenyl ethers (for the production of intermediates in carotenoid syntheses) and acylations of phenols.

The reaction of 4-hydroxy-2-methyl-naphthalen-1-yl benzoate with isophytol to give 4-hydroxy-2-methyl-3-(3,7,11,15-tetramethyl-hexadec-2-enyl)-naphthalen-1-yl benzoate (dihydro-vitamin $K_1$ monobenzoate) and of trimethylhydroquinone with isophytol to give d,l-α-tocopherol (vitamin E) can be mentioned as examples of Friedel-Crafts condensations, the reaction of acetaldehyde dimethyl acetal or (E)-1,1,4,4-tetramethoxy-but-2-ene with methyl propenyl ether or of 13-(2,6,6-trimethyl-cyclohexen-1-yl)-2,7,11-trimethyl-trideca-2,6,8,10,12-pentaen-4-yn-1-al diethyl acetal with ethyl vinyl ether can be mentioned as examples of vinyl ether condensations of acetals with vinyl or propenyl ethers for the production of intermediates in carotenoid syntheses, and the production of d,l-α-tocopherol acetate from d,l-α-tocopherol can be mentioned as an example of acylations of phenols.

Various processes for performing Friedel-Crafts condensations have already been described in the literature and are carried out using protonic acids, such as hydrohalic acids, e.g. hydrochloric acid, trichloroacetic acid and the like, Lewis acids, such as aluminium chloride, boron trifluoride, iron chloride, zinc chloride and the like, or mixtures of the two types of acid, such as a mixture of zinc chloride and a strong protonic acid and the like, as catalysts.

All of these previously known processes have serious disadvantages. For example, corrosion problems occur in all processes, and when boron trifluoride is used toxicity problems arise with the boron trifluoride adducts. Also, when iron or zinc is used there is a contamination of the waste water with iron or zinc ions which today is no longer acceptable.

Since vinyl ether condensations are usually carried out with Lewis acids, disadvantages as described above for the Friedel-Crafts condensations with Lewis acids also occur in the case of this type of reaction.

SUMMARY OF THE INVENTION

The object of the present invention is accordingly to provide a catalyst system for the aforementioned condensation reactions which does not have the disadvantages of the previously known procedures. It is thus necessary that such a catalyst system is not corrosive, is not toxic, does not pollute the environment and catalyzes the desired reaction as selectively as possible and in high yields. Moreover, the catalyst system should display this activity already in amounts which are truly only catalytic and should be readily separable.

In the scope of the present invention this object is achieved by using hydrogen bis(oxalato)borate of formula I above as the protonic acid catalyst in the condensation reactions.

DETAILED DESCRIPTION OF THE INVENTION

The condensations can be carried out in the presence or absence of a solvent at temperatures between about 0° C. and about 140° C. depending on the type of reaction (Friedel-Crafts condensation, vinyl ether condensation or acylation of phenols) and the starting materials which are used. Thus, the Friedel-Crafts condensation is carried out conveniently at temperatures between about 80° C. and about 140° C., preferably between about 85° C. and about 120° C., particularly at the reflux temperature of the reaction mixture. On the other hand, the vinyl ether condensations are conveniently carried out in the absence of a solvent at temperatures between about 0° C. and about 40° C., preferably between about 15° C. and about 25° C., particularly at about room temperature.

As suitable solvents in the scope of the present invention there can be mentioned aromatic hydrocarbons, e.g. toluene, xylene and the like, halogenated aromatic hydrocarbons, e.g. chlorobenzene and the like, aliphatic carboxylic acid esters, e.g. ethyl acetate, isopropyl acetate and the like, aliphatic ethers, e.g. methyl tert.butyl ether, diisobutyl ether and the like, as well as aliphatic and cyclic ketones having a boiling point between about 80° C. and about 140° C., e.g. diethyl ketone, methyl isopropyl ketone, cyclopentanone and the like. Toluene and isopropyl acetate are preferred.

In accordance with the invention the condensation can be carried out in the presence of about 0.1 to about 6, preferably about 0.2 to about 4, particularly about 0.3 to about 3, mol % of hydrogen bis(oxalato)borate as the catalyst (in each case based on the respective molar amount of starting material).

The hydrogen bis(oxalato)borate of formula I above is known from Journal of Organometallic Chemistry, 329, 1–29 (1987). It can be prepared as described in Example 1, whereby it is advantageously not prepared and used in situ, but in isolated form.

The following Examples illustrate the invention, but are not intended in any way to be a limitation. All temperatures are given in degrees Celsius.

EXAMPLE 1

13.96 g (150.36 mmol) of oxalic acid and 2.62 g (37.59 mmol) of diboron trioxide [or 8.4 ml (75.2 mmol) of trimethyl borate or 3.7 ml (25.1 mmol) of trimethoxyboroxine] were suspended in 450 ml of toluene in a 1 l flask and stirred under reflux for 6 hours, with the reaction water which resulted being separated continuously using a water separator. The cooled reaction mixture was subsequently filtered and the solid residue was dried in a vacuum, there being obtained hydrogen bis(oxalato)borate in 70% yield.

EXAMPLE 2

28.398 g (100 mmol) of 4-hydroxy-2-methyl-naphthalen-1-yl benzoate and 127.4 mg (0.569 mmol) of hydrogen bis(oxalato)borate were placed in 170 ml of toluene in a 500 ml sulphonation flask. The reaction mixture was heated to 98° and subsequently treated with 17.76 g (56.9 mmol) of isophytol within 15 seconds.

After completion of the addition the reaction mixture was stirred at 98° for a further 30 minutes. The yield of 4-hydroxy-2-methyl-3-[(E)-3,7,11,15-tetramethyl-hexadec-2-enyl]-naphthalen-1-yl benzoate was 80% (calculated on isophytol, direct LC determination from the reaction mixture on the basis of a standard curve).

EXAMPLE 3

35.240 g (200 mmol) of (E)-1,1,4,4-tetramethoxy-but-2-ene and 1.343 g (6 mmol) of hydrogen bis(oxalato)borate were placed in a 200 ml sulphonation flask while stirring. 28.840 g (400 mmol) of methyl propenyl ether were subsequently added dropwise at room temperature within 4 hours and, after completion of the addition, the mixture was left to react for a further 30 minutes.

The reaction solution was then treated with 300 ml of water and 2 ml of 15% hydrochloric acid, and the resulting methanol was distilled off. 12 ml of 15% sodium hydroxide solution were added within 15 minutes and the mixture was stirred at 80° for a further 30 minutes. The cooled reaction mixture was then filtered and dried, there being obtained 2,7-dimethyl-2,4,6-(E,E,E)-octatrienedial in 67% yield (LC analysis).

EXAMPLE 4

27.04 g (300 mmol) of acetaldehyde dimethyl acetal and 282 mg (1.26 mmol) of hydrogen bis(oxalato)borate were placed in a 100 ml sulphonation flask and then 7.21 g (100 mmol) of methyl propenyl ether were added dropwise at room temperature within 2 hours. After warming the reaction mixture to 40° for one hour it was left to cool to room temperature, with 1,1,3-trimethoxy-2-methyl-butane being obtained; the content of 1,1,3-trimethoxy-2-methyl-butane was 70% according to GC analysis.

EXAMPLE 5

A mixture of 5.0 g (14.3 mmol) of 13-(2,6,6-trimethyl-cyclohexen-1-yl)-2,7,11-trimethyl-trideca-2,6,8,10,12-pentaen-4-yn-1-al, 3.1 ml (18.2 mmol) of triethyl orthoformate, 0.8 ml of ethyl formate and 89.5 mg (0.4 mmol) of hydrogen bis(oxalato)borate was placed in a 100 ml sulphonation flask. The reaction mixture was stirred at 15° for 1 hour, subsequently treated dropwise at this temperature with 1.9 ml (19.7 mmol) of ethyl vinyl ether and stirred for a further 15 minutes. The yield of 13,15,15-triethoxy-3,7,12-trimethyl-1-(2,6,6-trimethyl-cyclohex-1-enyl)-pentadeca-1,3,5,7,11-pentaen-9-yne was 80%.

EXAMPLE 6

60.88 g (400 mmol) of trimethylhydroquinone and 2.81 g (12.53 mmol) of hydrogen bis(oxalato)borate were placed in 180 ml of toluene in a 750 ml sulphonation flask. The reaction mixture was subsequently heated to reflux under an argon atmosphere and 147.76 ml (400 mmol) of isophytol were then continuously added dropwise during 2 hours. After completion of the addition the reaction mixture was heated to reflux for a further 30 minutes and, after cooling, treated with 200 ml of hexane. The reaction mixture was subsequently extracted with methanol/water, there remaining behind after distillation of the solvent 104.5 g of crude d,l-α-tocopherol which had a content of 88.0% according to gas chromatographical analysis; yield 92%.

EXAMPLE 7

A mixture of 43.00 g (100 mmol) of tocopherol, 11.40 g (110 mmol) of acetic anhydride and 94 mg (0.5 mmol) of hydrogen bis(oxalato)borate was placed in a 100 ml sulphonation flask and the reaction mixture was heated to reflux under an argon atmosphere for one hour. After concentration on a rotary evaporator there remained behind 47.2 g of crude d,l-α-tocopherol acetate which had a content of 87%; yield 92%.

I claim:

1. A method of catalyzing a condensation reaction, whereby hydrogen bis(oxalato)borate of formula I

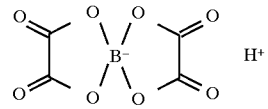

is used as a protonic acid catalyst and wherein the condensation reaction is one selected from the group consisting of a Fiedel-Crafts condensation, a vinyl ether condensation of an acetal with an ether selected from the group consisting of vinyl and propenyl ethers, and an acylation of a phenol wherein the forgoing reactions are optionally in the presence of a solvent.

2. A method of catalyzing a condensation reaction whereby hydrogen bis(oxalato)borate of formula I

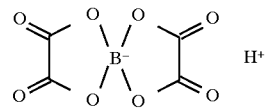

is used as a protonic acid catalyst and wherein the hydrogen bis(oxalato)borate of formula I is used in isolated form and the condensation reaction is one selected from the group consisting of a Friedel-Crafts condensation, a vinyl ether condensation of an acetal with an ether selected from the group consisting of vinyl and propenyl ethers, and an acylation of a phenol optionally in the presence of a solvent.

3. The method according to claim 2, wherein about 0.1 to about 6 mol % of hydrogen bis(oxalato)borate is used as the catalyst.

4. The method according to claim 2, wherein about 0.3 to about 3 mol % of hydrogen bis(oxalato)borate is used as the catalyst.

5. The method according to claim 1, wherein the Friedel-Crafts condensation is carried out at temperatures between about 80° C. and about 140° C.

6. The method according to claim 2, wherein the Friedel-Crafts condensation is carried out at temperatures between about 80° C. and about 140° C.

7. The method according to claim 1, wherein the Friedel-Crafts condensation is carried out at the reflux temperature of the reaction mixture.

8. The method according to claim 2, wherein the Friedel-Crafts condensation is carried out at the reflux temperature of the reaction mixture.

9. The method according to claim 2, wherein the catalyzation of the condensation reaction occurs in the presence of a solvent, said solvent being selected from the group consisting of an aromatic hydrocarbon, a halogenated aromatic hydrocarbon, an aliphatic carboxylic acid ester, an aliphatic ether and an aliphatic or cyclic ketone having a boiling point between about 85° C. and about 140° C.

10. The method according to claim 3, wherein the catalyzation of the condensation reaction occurs in the presence of a solvent, said solvent being selected from the group consisting of an aromatic hydrocarbon, a halogenated aromatic hydrocarbon, an aliphatic carboxylic acid ester, an aliphatic ether and an aliphatic or cyclic ketone having a boiling point between about 85° C. and about 140° C.

11. The method according to claim 2, wherein the catalyzation of the condensation reaction occurs in the presence of a solvent, said solvent being selected from the group consisting of an aromatic hydrocarbon, a halogenated aromatic hydrocarbon, an aliphatic carboxylic acid ester, an aliphatic ether and an aliphatic or cyclic ketone having a boiling point between about 85° C. and about 140° C.

12. The method according to claim 6, wherein the catalyzation of the condensation reaction occurs in the presence of a solvent, said solvent being selected from the group consisting of an aromatic hydrocarbon, a halogenated aromatic hydrocarbon, an aliphatic carboxylic acid ester, an aliphatic ether and an aliphatic or cyclic ketone having a boiling point between about 85° C. and about 140° C.

13. The method according to claim 9, wherein the solvent is selected from the group consisting of toluene, xylene, chlorobenzene, ethyl acetate, isopropyl acetate, methyl tert.butyl ether, diisobutyl ether, diethyl ketone, methyl isopropyl ketone and cyclopentanone.

14. The method according to claim 1, wherein the solvent is selected from the group consisting of toluene, xylene, chlorobenzene, ethyl acetate, isopropyl acetate, methyl tert.butyl ether, diisobutyl ether, diethyl ketone, methyl isopropyl ketone and cyclopentanone.

15. The method according to claim 2, wherein the solvent is selected from the group consisting of toluene, xylene, chlorobenzene, ethyl acetate, isopropyl acetate, methyl tert.butyl ether, diisobutyl ether, diethyl ketone, methyl isopropyl ketone and cyclopentanone.

16. The method according to claim 6, wherein 4-hydroxy-2-methyl-naphthalen-1-yl benzoate is reacted with isophytol.

17. The method according to claim 6, wherein trimethylhydroquinone is reacted with isophytol.

18. The method according to claim 2, wherein the vinyl ether condensation is carried out at temperatures between about 0° C. and about 40° C.

19. The method according to claim 2, wherein the vinyl ether condensation is carried out at about room temperature.

20. The method according to claim 18, wherein acetaldehyde dimethyl acetal is reacted with methyl propenyl ether.

21. The method according to claim 18, wherein (E)-1,1,4,4-tetramethoxy-but-2-ene is reacted with methyl propenyl ether.

22. The method according to claim 18, wherein 13-(2,6,6-trimethylcyclohexen-1-yl)-2,7,11-trimethyl-trideca-2,6,8,10,12-pentaen-4-yn-1-al diethyl acetal is reacted with ethyl vinyl ether.

* * * * *

UNITED STATES PATENT AND TRADEMARK OFFICE
CERTIFICATE OF CORRECTION

PATENT NO. : 5,886,196
DATED : March 23, 1999
INVENTOR(S) : CLAUDE FÜRBRINGER

It is certified that error appears in the above-identified patent and that said Letters Patent is hereby corrected as shown below:

In the title page [75], delete "Sweden" and insert therefor -- Switzerland --.

In the title page [30], delete "Sweden" and insert therefor -- Switzerland --.

In Column 4, line 30, (claim 2, last line), after "phenol" and before "optionally" insert -- wherein the foregoing reactions are --.

Signed and Sealed this

Seventh Day of September, 1999

Attest:

Q. TODD DICKINSON

Attesting Officer    Acting Commissioner of Patents and Trademarks